United States Patent [19]

Umezawa et al.

[11] 4,335,250

[45] Jun. 15, 1982

[54] COMPOUND WITH IMMUNOPOTENTIATING ACTIVITY AND PRODUCTION AND USES THEREOF

[75] Inventors: Hamao Umezawa; Tomio Takeuchi, both of Tokyo; Takaaki Aoyagi, Fujisawa; Masaaki Ishizuka, Tokyo; Hajime Morishima, Tokyo; Takuzo Yamamoto, Tokyo; Junji Yoshizawa, Tokyo; Masaaki Hosoi, Kawasaki; Ikuo Matsumoto, Tokyo, all of Japan

[73] Assignee: Banyu Pharmaceutical Co., Ltd., Tokyo, Japan

[21] Appl. No.: 57,014

[22] Filed: Jul. 12, 1979

[30] Foreign Application Priority Data

Jul. 17, 1978 [JP] Japan .................................. 53/86178

[51] Int. Cl.³ ............................................. C07C 69/88
[52] U.S. Cl. ..................................... 560/67; 562/475;
424/308; 424/317; 260/501.1; 260/501.17
[58] Field of Search .......................... 560/67; 562/475;
424/308, 317

[56] References Cited

U.S. PATENT DOCUMENTS 3,496,211 2/1970 Dexter et al. .......................... 560/67

FOREIGN PATENT DOCUMENTS 1114223 5/1968 United Kingdom .................. 560/67

OTHER PUBLICATIONS

Carter, J. E. et al., J. Pharamaceutical Sciences, vol. 66, No. 4, Apr. 1977.

Primary Examiner—Paul J. Killos
Attorney, Agent, or Firm—Larson and Taylor

[57] ABSTRACT

A new compound is produced which has the general formula:

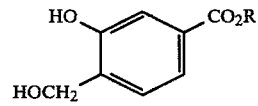

wherein R represents hydrogen atom or a lower alkyl group and which exhibits an immunopotentiating activity. This new compound as well as its pharmaceutically acceptable salts and hydrates are useful for immunotherapy and treatment of immune diseases and disorders in living animals including human beings. The new compound can be produced by reduction of a hydroxyterephthalic acid alkyl ester or by esterification of the corresponding 3-hydroxy-4-(hydroxymethyl)-benzoic acid.

7 Claims, No Drawings

NEW COMPOUND WITH IMMUNOPOTENTIATING ACTIVITY AND PRODUCTION AND USES THEREOF

SUMMARY OF THE INVENTION

This invention relates to new compounds having immunopotentiating properties, to processes for the production thereof and to uses thereof as immunopotentiator or for enhancing immunological response in animals and humans.

BACKGROUND OF THE INVENTION

We have studied in search of useful derivatives of a known compound, forphenicine having the following structure:

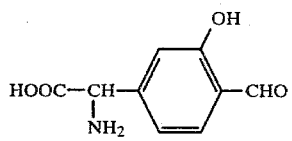

Forphenicine is a known substance which was first isolated from the culture broth of a strain of actinomycetes by H. Umezawa et al. and which is active as a strong inhibitor alkaline phosphatase and enhances delayed-type hypersensitivity and increases the number of antibody-forming cells (Japanese Patent Prepublication "Kokai" No. 116685/75, "Journal of Antibiotics" Vol. 31, No. 3, pp. 244–246 and Vol. 31, No. 5, pp. 483–484 (1978) as well as Vol. 30, Suppl. S-153 (1977)).

We have already discovered a useful derivative of forphenicine of the structural formula:

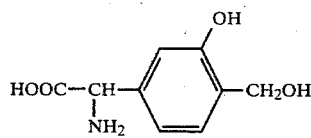

This compound is designated as forphenicinol and is found to have an immunopotentiating activity (see Japanese Patent Pre-publication No. 44632/79 published on Apr. 9, 1979; and co-pending U.S. patent application Ser. No. 21,222, now U.S. Pat. No. 4,238,507.

In the course of our further studies, we have now found new related compounds of the general formula:

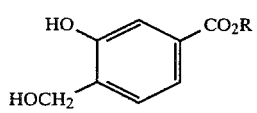

and salts and hydrates thereof, wherein R represents hydrogen atom or a linear or branched lower alkyl group. These compounds have been observed to possess immunopotentiating activity and are thus useful as an immunopotentiator for enhancing the immune response in living animals and humans.

An object of this invention is to provide new compounds which exhibit immunopotentiating activities. Another object of the invention is to provide processes of producing these new, useful compounds. Further object of the invention is to provide an immunopotentiator or antitumor agent comprising these compounds.

Other objects and utilities of the invention will become apparent from the following descriptions.

DETAILED DESCRIPTION OF THE INVENTION

According to a first aspect of this invention, therefore, there is provided a new compound of the general formula:

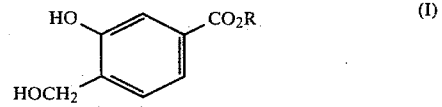

and its pharmaceutically acceptable salts and hydrates and salts thereof, wherein R represents hydrogen atom or a linear or branched lower alkyl group, for example, methyl, ethyl or propyl group. The term "lower alkyl" used herein means an alkyl containing 1 to 4 carbon atoms.

Typical Examples of the compound of above formula (I) include 3-hydroxy-4-(hydroxymethyl)benzoic acid (R being hydrogen), methyl 3-hydroxy-4-(hydroxymethyl) benzoate (R being methyl) and ethyl 3-hydroxy-4-(hydroxymethyl) benzoate (R being ethyl).

The pharmaceutically acceptable salts of the compound (I) according to this invention include salts with an alkali metal such as sodium and potassium; with alkaline earth metal such as calcium and magnesium; and with an organic amine such as trialkylamine, dicyclohexylamine and the like.

In a second aspect of this invention, there is provided a process for the production of the compound of above general formula (I), which comprises selectively reducing a compound of the general formula:

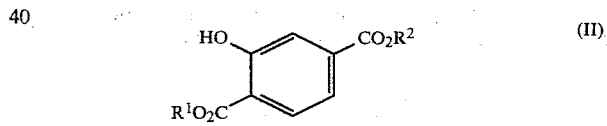

wherein $R^1$ represents a linear or branched alkyl group and $R^2$ represents hydrogen atom or a linear or branched lower alkyl group so as to convert the carboxylic acid ester group adjoining the hydroxyl group (as shown above) of the compound (II) into hydroxymethyl group.

Examples of the starting compound (II) to be used in the process includes dimethyl hydroxyterephthalate and diethyl hydroxyterephthalate.

The reduction may be carried out under appropriate reaction conditions using a reducing agent which may be a metal hydride complex, for example, sodium borohydride, sodium dihydro-bis-(2-methoxyethoxy) aluminate or lithium aluminumhydride.

In a typical embodiment of the process, the reduction may be effected at ambient temperature or an elevated temperature in an inert solvent, preferably a lower alkanol such as methanol or ethanol, using sodium borohydride as reducing agent. Where sodium dihydro-bis-(2-methoxyethoxy) aluminate is used as reducing agent, the reaction may take place at ambient temperature or a lower temperature in an organic solvent inert to the reaction, usually benzene or toluene. With lithium aluminumhydride, the reduction may be suitably carried out under ice-cooling in an inert solvent for the reducing agent, for example, tetrahydrofuran or ethyl ether.

The amount of the reducing agent to be used will depend on the nature of the reducing agent, the reaction temperature employed and the nature of the solvent to be generally used. An appropriate amount of a particular reducing agent can be determined by simple routine experiments. By way of general guidance, however, sodium borohydride may be used in one to ten molar ratio conveniently about five to ten molar ratio with respect to the starting compound (II) and sodium dihydrobis-(2-methoxyethoxy) aluminate lithium aluminumhydride may be used in about one or two molar ratio to the starting compound (II). In this way, the carboxylic ester group adjacent to the hydroxyl group of the compound (II) can preferentially be reduced into the hydroxymethyl group.

The compound of above formula (I) in which R is hydrogen atom, namely 3-hydroxy-4-(hydroxymethyl) benzoic acid can be produced by the reduction with a metal hydride complex of the starting compound (II) where $R^2$ is hydrogen atom, in a manner as noted just above, or alternatively by the selective reduction with a metal hydride complex of the starting compound of above formula (II) where both $R^1$ and $R^2$ represent linear or branched lower alkyl group so as to convert preferentially the carboxylic acid ester group adjacent to the hydroxyl group into hydroxymethyl group, followed by hydrolysis of the remaining ester group into carboxyl group. The hydrolysis may be performed by any conventional method, preferably by a method using an alkali or alkaline earth metal hydroxide, e.g. sodium or barium hydroxide in a solvent mixture of water and a water-miscible solvent such as methanol at ambient temperature or an elevated temperature.

In an alternative way, the compound of general formula (I) in which R is a linear or branched lower alkyl group can be prepared by esterifying the corresponding carboxylic acid compound of the formula:

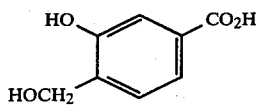

The esterification may be effected by reacting with an alkanol of 1-4 carbon atoms according to any conventional method known in the art.

As already stated, the new compounds of general formula (I) and pharmaceutically acceptable salts and hydrates thereof exhibit immunopotentiating activities. As is clearly seen from the test results set out in Examples hereinafter, the compounds of the invention have an inhibitory effect on the growth of various animal transplantable tumors. Since the compounds of the invention have no cytotoxicity, it is estimated that the inhibitory effect of the compounds on tumor growth is due to the activation of host defence mechanisms.

The new compounds of the invention exhibit an $LD_{50}$ value of more than 500 mg/kg when intraperitoneally injected into mice.

It is thus found that the compounds are useful for immunotherapy and chemotherapy for cancer, immunodeficiency in tomor-bearing host and inhibition of metastasis of cancer. Further, the compounds can be effectively used for treatment of diseases and disorders which may be induced by immunodeficiency, for example, rhenmatoid, multiple sclerosis, collagen disease and systemic lupus erythematodes.

According to a further aspect of this invention, there is provided a process of potentiating the immune response in a living animal including man, which comprises administering orally or parenterally into the animal an effective amount of a compound of above general formula (I) or a pharmaceutically acceptable salt or hydrate thereof.

This invention also provides a pharmaceutical composition, useful as immunopotentiator and antitumor agent, comprising as active ingredient a compound of above general formula (I) or a pharmaceutically acceptable salt or hydrate thereof a salt of the hydrate, in combination with a pharmaceutically acceptable carrier or adjuvant for the active ingredient. The composition may comprise the active ingredient at a concentration varying within a wide range, for example, of 1 to 90% by weight.

The composition of the invention may be formulated for oral or parenteral administration. Compositions in the form of injectable solution may contain 0.1% to 10% by weight of the active ingredient, and also one or more of a pH adjustor, buffer, stabilizer, excipient, local anesthetics and an additive for rendering the solutions isotonic. The injectable solutions may be prepared to be adapted for subcutaneous, intramuscular or intravenous injection by any conventional technique. If desired, the solutions may be lyophilized in a usual manner to prepare lyophilized injections.

Solid compositions for oral administration, which may be in the form of tablets, coated tablets, granules, powders and capsules, may contain excipients for the active ingredients and, if required, other additives including binders, disintegrators, lubricants, colorants, sweetening agents and flavorings.

Liquid compositions for oral administration, which may be in the form of syrups and dry syrups, may also contain sweetening agents, buffers, stabilizers, flavorings and the like.

Suppository formulations may contain excipients and, if necessary, surfactants in addition to the active ingredients.

The dosage of the compound (I) administered will, of course, depend on the mode of administration and the treatment desired. For men, the unit dosage generally comprises from 0.02 mg to 200 mg of the compound (I), which may be administered once a day or in divided doses two or more times per day.

This invention is further illustrated but not limited by the following Examples.

EXAMPLE 1

Preparation of methyl 3-hydroxy-4-(hydroxymethyl) benzoate 580 mg of dimethyl hydroxyterephthalate was dissolved in 30 ml of absolute methanol and 2.5 g of sodium borohydride was slowly added to the solution. After completion of the addition, the mixture was agitated at room temperature for one hour and then adjusted under ice-cooling to pH 1.95 with 6 N hydrochloric acid, followed by extraction with butanol. The extract was evaporated to remove the solvent, the residue was taken up in benzene and the solution was passed through a column of 100 ml of silica gel (Kieselgel 60 made by Merck Co.) which had been suspended in benzene. The column was washed with 1000 ml of a mixture of benzene-ethyl acetate (9:1 by volume) and then eluted with 750 ml of a mixture of benzene-ethyl acetate (4:1 by volume). The eluate was collected in fractions of each 15 g and fraction Nos. 41–85 containing the desired compound were combined together and concentrated to dryness, yielding 418 mg (83%) of the desired product. Recrystallization from a mixture of benzene-methanol-ethyl ether gave 320 mg of the titled compound as colorless crystals with a melting point of 104.5°–105° C.

Infrared absorption spectrum:

$\nu_{max}^{KBr}$ (cm$^{-1}$): 3430, 3200, 2920, 1708, 1695, 1612, 1590, 1517, 1440, 1420, 1370, 1360, 1310, 1295, 1280, 1255, 1235, 1220, 1190, 1178, 1110, 1095, 1030, 978, 950, 923, 880, 872, 840, 805, 790, 756

Nuclear magnetic resonance spectrum (60 MHz, in dentero methanol):

$\delta_{ppm}^{TMS}$: 3.88 (3H, S), 4.72 (2H, S), 7.3–7.7 (3H)

EXAMPLE 2

Preparation of 3-hydroxy-4-(hydroxymethyl) benzoic acid 316 mg of methyl 3-hydroxy-4-(hydroxymethyl) benzoate prepared as described in Example 1 was dissolved in 1 ml of methanol, to which was then added 5 ml of 1 N aqueous sodium hydroxide. The mixture was allowed to stand at room temperature for 1.5 hours to effect the saponification. Thereafter, the reaction mixture was diluted with water, admixed with 5 ml of 1 N hydrochloric acid and then extracted with ethyl acetate. The extract was evaporated under reduced pressure to remove the solvent, yielding 272 mg (93%) of the desired product. Recrystallization from a mixture of benzene-ethanol gave 154 mg of the titled compound as colorless crystals.

Melting point: 173.5°–174.5° C. (with decomposition)

I.R. spectrum:

$\nu_{max}^{KBr}$ (cm$^{-1}$): 3390, 3080, 2960, 2880, 2800, 2700 2150, 1660, 1615, 1588, 1520, 1425, 1395, 1365, 1303, 1248, 1195, 1125, 1098, 1033, 982, 940, 888, 850, 793, 770, 760

N.M.R. spectrum (60 MHz, in deutero dioxane+-deutero water)

$\delta_{ppm}^{TMS}$: 4.68 (2H, S), 7.35–7.6 (3H)

EXAMPLE 3

Preparation of ethyl 3-hydroxy-4-(hydroxymethyl)benzoate

Following the procedure as described in Example 1, the titled compound was obtained starting from diethyl hydroxyterephthalate.

Melting point: 92°–94° C.

Elemental analysis: Found: C, 61.14; H, 6.24%. Calcd. for $C_{10}H_{12}O_4$: C, 61.21; H, 6.17%.

Ultraviolet absorption spectrum:

$\lambda_{max}^{EtOH}$ (NM): 213 ($\epsilon$25000), 245 ($\epsilon$10000), 300($\epsilon$3500)

I.R. spectrum:

$\nu_{max}^{KBr}$ (cm$^{-1}$): 3430, 3140, 1675, 1585, 1420, 1290, 1235, 1090, 1035, 1010, 985, 945, 890, 825, 765

N.M.R. spectrum (60 MHz, in deutero dimethylsulfoxide)

$\delta_{max}^{TMS}$: 1.30 (3H, t), 4.26 (2H, q), 4.55 (2H, s), 5.10 (1H, s), 7.44 (3H, s), 9.70 (1H, s)

EXAMPLE 4

10 g of a compound of formula (I) was dissolved in distilled water to give 1000 ml of the solution, which was sterilized in a conventional manner. The sterilized solution was charged in 2 ml portions into vials and lyophilized. The formulation so obtained is diluted with distilled water before use to give an injectable solution.

EXAMPLE 5

One part of a compound of formula (I), 200 parts of lactose and 50 parts of corn starch were mixed together and the mixture was granulated with addition of ethanol, dried and then screened in a usual manner. The granules obtained were admixed with 0.5% magnesium stearate as lubricant and the admixture was shaped into tablets of each 3.6 mg weight by a conventional technique.

EXAMPLE 6

One part of a compound of formula (I) was thoroughly mixed with 900 parts of lactose and the mixture was screened with a 50 mesh sieve to form powders.

The following Examples 7–10 illustrate the immunopotentiating properties of 3-hydroxy-4-(hydroxymethyl) benzoic acid (hereinafter referred to as BF-127 substance) which is representative of the compounds (I) of this invention.

EXAMPLE 7

In this Example, the effect of BF-127 substance on cellular immunity (cell-mediated immunity) was tested according to a known Delayed-Type Hypersensitivity (D.T.H.) technique (see P. H. Lagrange, G. B. Mackaness and T. E. Mille, "J. Exp. Med", 139, 1529–1539 (1974) using mice immunized with sheep red blood cells as antigen.

Thus, $10^8$ sheep red blood cells (SRBC) suspended in 0.05 ml of physiological saline were subcutaneously injected at the time of immunization to the right hind footpad of each ICR mouse under test (female, 6 weeks aged) to establish delayed-type hypersensitivity. Simultaneously with the immunization, a varying dose of BF-127 substance was intraperitoneally injected into each test mouse. Four days later, $10^8$ sheep red blood cells were subcutantaneously injected into the left hind footpad of each test mouse for elicitation of the D.T.H. response. 24 hours after eliciting injection, the thickness of the left hind footpad was measured with a vernier caliper to evaluate the degree of the resulting edema in the footpad. The degree of the swelling serves to estimate the cellular immunity involved. The test results obtained are set out in Table 1 below. In the Table, the swelling degree is expressed in terms of the values calculated by the equation:

$$\frac{\text{Thickness of the footpad of mouse treated with } BF\text{-127 substance}}{\text{Thickness of the footpad of mouse untreated}} \times 100$$

TABLE 1

| Dose of BF-127 | Increase in thickness of footpad (× 0.1 mm) | Swelling degree (%) |
| --- | --- | --- |
| 0 (control) | 8.3 ± 1.0 | — |
| 1 mg/mouse | 13.1 ± 0.4 | 158 |
| 100 μg/mouse | 15.7 ± 0.3 | 189 |
| 10 μg/mouse | 15.5 ± 1.3 | 187 |

TABLE 1-continued

| Dose of BF-127 | Increase in thickness of footpad (× 0.1 mm) | Swelling degree (%) |
|---|---|---|
| 1 μg/mouse | 19.4 ± 1.8 | 234 |
| 0.1 μg/mouse | 14.3 ± 1.1 | 172 |

The above results show that administration of BF-127 subtance at doses of 1 mg to 0.1 μg/mouse potentiates the DTH response by 58 to 134% as compared with the control, and thus it is revealed that BF-127 substance brings about an intensive potentiating effect on establishment of cellular immunity.

Such potentiating effect has also been observed upon oral administration as well as upon intravenous and subcutaneous injections of BF-127 substance. By way of reference, the test results conducted by the same procedure as above except that BF-127 substance was orally administered are indicated in Table 2 below.

TABLE 2

| Dose of BF-127 | Swelling degree (%) |
|---|---|
| 1 mg/mouse | 133 |
| 100 μg/mouse | 148 |
| 10 μg/mouse | 146 |

The above results show that the DTH response is potentiated by 30–50% upon oral administration of BF-127 substance at doses of 1 mg to 10 μg/mouse.

EXAMPLE 8

This Example reveals that the immunopotentiating effect of BF-127 substance is also observed with other strains of mice of different ages.

The same test procedure as described in Example 7 was repeated but using $CDF_1$ (DBA/2xBALB/$CF_1$) male mice (9 weeks old), in which varying doses of BF-127 substance were intraperitoneally injected or orally administered into each test mouse. The tests results are shown in Table 3 below where the swelling degree has the same significance as in Example 7.

TABLE 3

| Dose of BF-127 | Swelling degree (%) | |
|---|---|---|
| | I.P. injection | Oral administration |
| 1 mg/mouse | 125 | 138 |
| 100 μg/mouse | 133 | 142 |
| 10 μg/mouse | 131 | 122 |
| 1 μg/mouse | 129 | 115 |
| 0.1 μg/mouse | 119 | 103 |

EXAMPLE 9

This Example illustrates the effect of BF-127 subtance on animal transplantable tumors.

$10^5$ Gardner Lymphoma cells were transplanted subcutaneously to the inguinal of each C3H/He mouse under test (female, 10 weeks old, 5 mice per group). 7 days after transplantation, a varying dose of BF-127 substance was intraperitoneally injected into each test mouse once a day for five successive days. 30 days after transplantation, the tumors formed were removed from the mice and weighed to evaluate the inhibitory effect of BF-127 substance on tumor growth in terms of average weight of the tumors formed in 5 mice. The results are tabulated in Table 4 below. For comparison, the results obtained with Bleomycin (Anti-tumor antibiotic made by Nihon Kayaku K.K., Japan) instead of BF-127 substance are also shown as control.

TABLE 4

| Dose of BF-127 | Average weight of tumors (mg) | Inhibition (%) |
|---|---|---|
| 0 (Untreated) | 1310 | — |
| 10 μg/mouse | 570 | 56.5 |
| 1 μg/mouse | 930 | 29.0 |
| 0.1 μg/mouse | 950 | 27.5 |
| Bleomycin 100 μg/mouse (Control) | 760 | 42.0 |

The above results indicate that administration of BF-127 substance at a dose of 10 μg/mouse can inhibit the growth of tumors to an extent superior or comparable to Bleomycin.

EXAMPLE 10

This Example illustrates the inhibitory effect of BF-127 substance on IMC Carcinoma. IMC Carcinoma is available from Microbial Chemistry Research Foundation, Tokyo, Japan, and is a sort of ascites tumors which was spontaneously induced in $CDF_1$ mice and has been successively transplanted in the same strain of mice. Pathological studies have shown that the above tumor is a sort of epithelial undifferentiated tumors.

$5 \times 10^6$ IMC tumor cells were transplanted hypodermically to the inguinal section of each $CDF_1$ mouse under test (female, 14 weeks old, 5 mice per group). 8 days after transplantation, a varying dose of BF-127 substance was intraperitoneally injected into each test mouse once a day for five successive days. 30 days after transplantation, the tumor formed were removed and weighed to evaluate the inhibitory effect of BF-127 substance on tumor growth in terms of average weight of the tumors formed in 5 mice.

The test results are set out in Table 5A. By way of comparison, the results obtained with known anti-tumor agents, Mytomycin (MMC) and Bleomycin (BLM) instead of BF-127 substance are also indicated as control.

Further tests were conducted following the procedure as above wherein $1 \times 10^6$ IMC tumor cells were inoculated and BF-127 substance was intraperitoneally injected (I.P.) or orally administered (P.O.). The results obtained are shown in Table 5B.

TABLE 5A

| Dose of BF-127 | Average weight of tumors (mg) | Inhibition (%) |
|---|---|---|
| 0 (Untreated) | 12380 | — |
| 100 μg/mouse | 7970 | 35.6 |
| 10 μg/mouse | 6190 | 50.0 |
| 1 μg/mouse | 5740 | 53.6 |
| BLM 100 μg/mouse (Control) | 5770 | 53.4 |
| MMC 20 μg/mouse (Control) | 5510 | 55.5 |

TABLE 5B

| Dose of BF-127 | Average weight of tumors (mg) | Inhibition (%) |
|---|---|---|
| 0 (Untreated) | 5635 | — |
| 10 μg/mouse (I.P.) | 1312 | 76.8 |
| 1 μg/mouse (I.P.) | 2206 | 60.8 |
| 10 μg/mouse (P.O.) | 2638 | 53.0 |
| 1 μg/mouse (P.O.) | 2538 | 55.0 |

What we claim is:
1. A compound of the general formula:

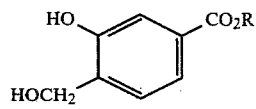

wherein R represents hydrogen atom or a linear or branched lower alkyl proup, and pharmaceutically acceptable salts and hydrates of the compound and pharmaceutically acceptable salts of the hydrates.

2. A compound according to claim 1 which is the compound of the formula (I) where R represents hydrogen atom.

3. A compound according to claim 1 which is the compound of the formula (I) where R represents methyl group.

4. A compound according to claim 1 which is the compound of the formula (I) where R represents ethyl group.

5. A pharmaceutical composition useful as immunopotentiator and immune antitumor agent, comprising as active ingredient a compound of the formula:

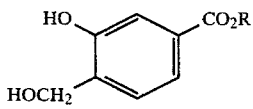

wherein R represents hydrogen atom or a linear or branched lower alkyl group or a pharmaceutically acceptable salt or hydrate thereof, in combination with a pharmaceutically acceptable carrier or adjuvant.

6. A process of potentiating the immune response in a living animal including man, which comprises administering orally or parenterally into the animal an effective amount of a compound of the formula:

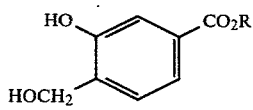

wherein R represents hydrogen atom or a linear or branched lower alkyl group or a pharmaceutically acceptable salt or hydrate thereof.

7. A process according to claim 6 in which the compound is administered into man at a unit dosage of 0.02 to 200 mg once a day or two or more times per day.

* * * * *